(12) United States Patent
Woldemichael (10) Patent No.: US 8,481,947 B2
(45) Date of Patent: Jul. 9, 2013

(54) METHOD AND SYSTEM FOR NUCLEAR IMAGING USING MULTI-ZONE DETECTOR ARCHITECTURE

(76) Inventor: Tilahun Woldeselassie Woldemichael, Oakland, CA (US)

( * ) Notice: Subject to any disclaimer, the term of this patent is extended or adjusted under 35 U.S.C. 154(b) by 601 days.

(21) Appl. No.: 12/706,707

(22) Filed: Feb. 16, 2010

(65) Prior Publication Data

US 2011/0073764 A1    Mar. 31, 2011

Related U.S. Application Data

(60) Provisional application No. 61/246,918, filed on Sep. 29, 2009.

(51) Int. Cl.
*G01T 1/20* (2006.01)
(52) U.S. Cl.
USPC .................................................. 250/362
(58) Field of Classification Search
USPC   235/362, 366, 396, 363.02, 363.03; 250/362, 250/366, 396, 363.02, 363.03
See application file for complete search history.

(56) References Cited

U.S. PATENT DOCUMENTS

| | | | |
|---|---|---|---|
| 5,539,202 A * | 7/1996 | Geagan et al. | 250/369 |
| 6,297,506 B1 | 10/2001 | Young | |
| 6,936,822 B2 | 8/2005 | Wong | |
| 7,132,664 B1 | 11/2006 | Crosetto | |
| 7,180,074 B1 | 2/2007 | Crosetto | |
| 7,217,928 B2 | 5/2007 | Crosetto | |
| 7,439,515 B2 * | 10/2008 | Bak | 250/369 |
| 2004/0195512 A1 | 10/2004 | Crosetto | |
| 2007/0057191 A1 | 3/2007 | Ueno | |
| 2007/0152163 A1 | 7/2007 | Yanagita | |
| 2007/0263764 A1 | 11/2007 | Mccallum | |
| 2008/0265887 A1 | 10/2008 | Linz | |
| 2008/0284428 A1 | 11/2008 | Fiedler | |
| 2009/0050816 A1 | 2/2009 | Amano | |

* cited by examiner

*Primary Examiner* — Edwyn Labaze
(74) *Attorney, Agent, or Firm* — Ariel S. Bentolila; Bay Area IP Group, LLC (57) ABSTRACT

A method and system for nuclear imaging normally involve detection of energy by producing at most two or three bursts of photons at a time in response to events including incident gamma radiation. F number of sharing central groups of seven photodetectors, depending on the photodetector array size, is arranged in a honeycomb array for viewing zones of up to F bursts of optical photons at a time for each continuous detector and converting the bursts of optical photons into signal outputs, where each of the central groups is associated with a zone. This enables the detector sensitivity to be increased by as much as two orders of magnitude, and to exchange some of this excess sensitivity to achieve spatial resolution comparable to those in CT and MRI, which would be unprecedented. Signal outputs that are due to scattered incident radiation are rejected for each of the central groups to reduce image blurring, thereby further improving image quality. For planar imaging, the energy and position signals of up to the F number of valid events are generated once every deadtime period and transferred to computer memory for image display and data analysis. The number of valid events detected is up to 6F for SPECT and up to 3F for PET imaging.

20 Claims, 10 Drawing Sheets

METHOD AND SYSTEM FOR NUCLEAR IMAGING USING MULTI-ZONE DETECTOR ARCHITECTURE

CROSS-REFERENCE TO RELATED APPLICATIONS

The present Utility patent application claims priority benefit of the U.S. provisional application for patent Ser. No. 61/246,918 filed on Sep. 29, 2009 under 35 U.S.C. 119(e). The contents of this related provisional application are incorporated herein by reference for all purposes.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

The present invention relates generally to the field of radiation imaging with emphasis on medical applications to nuclear medicine. More particularly, the invention relates to a method and an apparatus for high resolution/sensitivity and improved image signal-to-noise ratio (SNR) for planar and tomographic (PET/SPECT) imaging.

BACKGROUND OF THE INVENTION

Medical imaging today includes radiography and computed tomography (CT) using x rays, nuclear imaging of injected or ingested radiopharmaceuticals using scintillation cameras and SPECT or PET scanners, magnetic resonance imaging (MRI) using strong magnetic fields, and ultrasound (US) imaging using high-frequency sound waves. With the exception of nuclear imaging, all the medical imaging modalities rely on the fact that the energy penetrating the body's tissues interacts with those tissues and the images provide anatomical, or structural, information about the tissues. In radiography, an external source produces an intense beam of x-rays, which is passed through the body, and as part of the beam is absorbed to varying degrees by different tissues, different parts of the film are sensitized to different degrees and an image of anatomical structure is obtained. In the case of nuclear imaging with gamma rays, the radiation is emitted by sources introduced into the body. Gamma rays differ from x-rays in that x-rays are emitted by orbital electrons in atoms, while gamma rays are emitted from within the nuclei of atoms and can also have considerably higher energies than x-rays. In nuclear imaging, the radiopharmaceuticals are formed by attaching a radioactive tracer to a pharmaceutical known to preferentially accumulate in the organ of interest. Since high-energy gamma radiation can penetrate bone and soft tissue alike, the pattern of the emerging radiation is a reflection of the distribution of the administered radiopharmaceutical, and provides functional information about blood flow, metabolism, or receptor density within the organ of interest.

Nuclear imaging is of two types, single-photon imaging and annihilation coincidence, or positron imaging. Single-photon imaging is used in gamma (or scintillation) cameras and in single-photon-emission computed tomography (SPECT), while annihilation coincidence imaging (ACD) is used in positron-emission tomography (PET). Nuclear images may be planar or tomographic, planar images essentially being two-dimensional maps of the radioisotope distribution, while single photon emission computed tomography (SPECT) is the tomographic counterpart of planar nuclear imaging, and produces an image of source distribution through a section of the body. In either case, x-rays or gamma-rays emerging from a series of different angles through the body are used to reconstruct a series of tomographic images. SPECT images enable physicians to make more accurate assessment of the functional state of specific organs or tissues within the body. The same radioactive isotopes are used in both planar and SPECT imaging. Since gamma rays from a source will be emitted equally in all directions, a parallel-hole lead collimator is needed to prevent the photons from reaching the detector by any path other than through the holes. The collimators typically consist of thick plates of lead with narrow parallel holes through which the gamma rays can pass. Gamma rays not traveling parallel to the holes are absorbed, or stopped by the lead before reaching the detector. Thus, if a collimator is placed over the body, a one-to-one correspondence between interaction points in the detector and the distribution of the isotope within the body can be established, which enables a planar image of this distribution to be obtained. If the collimator were to be removed, the gamma rays would reach the detector from all directions, and a uniformly white image with little information content would be obtained. In the case of positron-emission imaging, the gamma rays themselves do not come directly from the nucleus. The nucleus emits a positron, or positive electron, which has only a short half-life and annihilates with an orbital, or negative electron, resulting in the emission of a pair of oppositely-directed 511-keV gamma rays. The fact that the pair of gamma rays is always emitted along a straight line makes it unnecessary to use collimators as in single-photon imaging. It is only necessary to use two detectors placed on opposite sides of the positron source to determine the line along which the photons are emitted. Image reconstruction software used in PET then enables a tomographic image of the source distribution to be generated. A state-of-the-art PET scanner typically utilizes banks of discrete stationary detectors surrounding the patient, so that annihilation photon pairs can be recorded by detector pairs from all projection angles. Since the positions of the positron emitters lie along the lines of response (LOR) of the detector pairs, a parallel-hole collimator to limit the direction of the photons is not needed, and attenuation by the collimator is avoided. A PET scanner system is therefore more sensitive to the presence of radioisotopes than SPECT cameras, and enables more subtle pathologies to be detected.

Although nuclear imaging systems are unique in their ability to provide functional information, in contrast to the other imaging modalities, they have the disadvantage of having the lowest spatial resolution, spatial resolution being the size of the smallest object that can be resolved in the image. While MRI and CT imaging can typically provide resolutions of 1.0 and 0.4 mm, respectively, planar nuclear cameras or SPECT scanners provide resolutions of about 7 mm, while PET scanners provide a resolution of 4-6 mm. The lower spatial resolution of nuclear images, coupled with their inability to provide anatomical information, has led to the development of hybrid PET/CT or PET/MRI systems in a single gantry, with a single bed for the patient, making co-registration of the PET images with those of CT or MRI possible. The anatomical images from CT or MRI provide more accurate information regarding the locations of lesions in the organs of patients, CT images additionally also providing data for the attenuation correction of the PET data. It is evident that for the quality of nuclear images to be more competitive with those of CT and MRI, the detector systems for them require significant improvement in spatial resolution, sensitivity and image signal-to-noise (SNR).

Scintillation detectors emit visible light photons when gamma rays interact in a scintillator crystal. Nuclear images are built up by counting the number of gamma ray interactions for each pixel in the image, and image contrast arises from differences of count density in the image. Detection of a gamma ray interaction in a scintillator consists in converting the burst of visible light photons into electrical pulses using a photodetector, such as the photomultiplier tube (PMT) or a photodiode (PD), each provided with its own preamplifier (PA). The total energy released by a gamma ray is obtained by adding all the PA outputs of exposed PMTs in a summing amplifier (SA), whose output is a measure of the energy signal. Since the amplitude of the PA outputs is highest for those PMTs closest to the interaction point and decreases with distance, the spatial coordinates of this point are determined by using the PA outputs for locating the centroid of light absorption. The circuit used to generates the (x,y) coordinates, or position signals, is referred to as Anger position logic. A gamma ray can interact with the scintillator by depositing its energy all at once, that is, by photoelectric interaction, or in smaller fractions, by Compton scattering. Photoelectric interaction is analogous to a fast-moving billiard ball hitting a stationary ball and being stopped, and transferring all its kinetic energy to the stationary ball. In the case of a gamma ray, the energy is transferred to an orbital electron, which then immediately releases its energy in the form of light in a series of collisions with atoms within a short distance. For all practical purposes, the light can be considered to be emitted from the interaction point of the gamma ray. In photoelectric interaction the number of visible light photons, and hence the amplitude of the energy signal at the SA outputs is a maximum. Compton-scatter interaction, on the other hand, is analogous to the fast-moving billiard ball colliding with the stationary ball at a glancing angle, thus losing only part of its energy and changing its direction. The scattered gamma ray may interact with the scintillator at any distance from the initial point of interaction, or even escape from the scintillator crystal undetected. The energy signals of Compton-scatter events lies anywhere between the maximum and nearly zero. In practice, nuclear medicine images are created using those energy signals that are within 10% to 20% of the most probable energy signal magnitude, which is not necessarily the same as that of a photoelectric event. Valid energy signals are selected by applying the SA outputs to a pulse-height analyzer (PHA), which accepts only those signals within a chosen energy window.

Anger type scintillation cameras for planar imaging consist in a flat large-area detector viewed by an array of PMTs and associated electronics for the determination of the gamma-ray energy and the spatial coordinates of interaction points. Anger cameras are photon counting systems, or operate in pulse mode, so that images are acquired one interaction at a time. This is in contrast to current-mode operation in other modalities, in which images are acquired as part of a single operation. In the basic scintillation camera, only a single SA is provided, with the inputs being the PA outputs of all the PMTs in the detector, typically 37, 61, or 91 in number. A single SA for the whole detector means that only one gamma ray interaction at a time can be detected, and detector operation is in single-zone mode. Energy determination is achieved by summing the outputs of all the PMTs together, while the spatial coordinates are determined by generating four position signals, usually referred to as the X+, X−, Y+, and Y− signals. The X+ and X− signals are obtained by summing the outputs of the PMTs in the right and left halves of the PMT array, respectively, while the Y+ and Y− signals are obtained by similarly summing the outputs of the upper and lower halves of the PMT array, respectively The X and Y coordinates of each event are then obtained taking X=(X+)−(X−) and Y=(Y+)−(Y−), normalized to (X+)+(X−) and (Y+)+(Y−), respectively. It is therefore inevitable that the determination of the photon energy and the spatial coordinates becomes susceptible to noise from PMTs at large distances from the interaction point. Furthermore, the fact that each event detected involves the entire array of PMTs in the detector, and that only one interaction at a time can be detected, remains one of the major shortcomings of the conventional scintillation camera. Two or more interactions in the detector lead to energy signal that are too large and fall outside of the energy window, and are therefore rejected. A source of image blurring is when two or more Compton-scatter interactions at different points in the detector occur simultaneously and the energy signals add up to that corresponding to photoelectric interaction. The composite energy signal would then be accepted by the PHA as valid, the Anger positioning logic circuitry generating the coordinates of an intermediate location between the Compton-scatter interactions as being the site of a photoelectric interaction. These events are referred to as misplaced pileup events, since a photoelectric interaction has not occurred there, the effect of these events being to blur the image of the radiopharmaceutical distribution. Considerable effort and research has been devoted to increasing the number of gamma-ray interactions that can be detected at a time. One solution adopted in state-of-the-art nuclear cameras is to dispense with the SA, digitize each of the PA output of the PMTs individually in separate analog-to-digital converters (ADCs) and read the data into computer memory. A computer program then analyzes the data to identify groups of PA outputs that correspond to valid gamma-ray interactions. This technique has helped in that up to three events at a time can now be detected, and cameras that operate in this way are referred to as digital cameras. Digital cameras are therefore often advertised as having one ADC per PMT to reflect this improvement in performance. Another approach to gamma camera design that overcomes the limitations of single-zone operation is one in which the detector is divided into multiple geographical zones, each of which is provided with an SA and Anger position logic, and operates independently, so that multiple events can be detected. This approach, however, is also limited to detecting at most only three valid events at a time. The large number of valid interactions that continues to be rejected, therefore, still remains a significant disadvantage.

Detector crystals for PET are considerably thicker than for single-photon imaging due to the higher energy of positron annihilation gamma rays. Additionally, the fact that collimators are not used in PET, and that the gamma rays can also reach the detectors at oblique angles means that the greater the angle of incidence, the greater the distances that can be traversed by the gamma rays in the crystal. Image reconstruction software in PET assumes that the scintillation event occurs directly below the point of initial incidence on the crystal surface, which is very rarely the case. Mispositioning of scintillation events in this way leads to image blurring referred to as depth-of-interaction (DOI) error. Thus, thick detectors for PET have the attendant problems of lower spatial resolution and significant DOI blurring of the image. The resolution of PET images is currently better than those of planar images because PET detector modules as a rule are divided into small segments typically 3×3×30 mm$^3$ to improve spatial resolution by limiting the divergence of the scintillation light once a gamma-ray interaction in a segment has taken place. Detector segmentation, however, has no effect on DOI error since the high energy gamma rays are able to penetrate the segments regardless.

Another important feature of nuclear imaging systems is count-rate capability, which is directly related to the detector's deadtime. Imaging applications can involve patient movement or fast redistribution of the radiopharmaceutical within the body, which can lead to blurred images unless an image can be built up in the shortest possible time. The shortest interval between individual detected events in the scintillation camera is referred to as its deadtime. The deadtime covers the period between the gamma-ray interaction in the crystal and the transfer of digitized energy and positional information to computer memory. There are two types of deadtime, the paralyzable deadtime of the detector, which is a characteristic of the scintillator decay time, and nonparalyzable deadtime, which is the time needed by the signal-processing hardware and the computer interface to generate and transfer the digital data into computer memory. Nonparalyzable deadtime is generally longer, but remains constant, while paralyzable deadtime increases with count-rate. The count rate for a paralyzable detector therefore increases only up to a peak value, which is proportional to the reciprocal of its deadtime $\tau_0$, and then decreases as count rate increases, eventually leading to detector paralysis. This occurs because, when one scintillation event follows immediately after the previous one, they merge together and the energy signals pile up in the SA, leading to the rejection of both by the PHA. Pile-up rejection becomes more frequent and the deadtime longer as the count rate increases. The way in which detector paralysis is prevented in existing imaging systems is by limiting the count rate, and consequently also the dose of administered radiopharmaceutical. The count-rate is rarely increased above the 20% count loss point, which means that only 80% of the peak count rate can be attained. The inefficient use of the detector and PMT array has long been recognized and has been receiving considerable attention. However, as noted earlier, it has not been practical to increase detector sensitivity by more than a factor of two or three times, as only two or three events per deadtime period can be recorded.

PET imaging requires that the interaction times of events in a coincidence pair be compared in order to establish a temporal overlap before use in image reconstruction. Current designs compare the interaction times of individual events against a master clock and store the time stamps along with the energy and spatial coordinates, once coincident events have been detected. The time window for coincidences is significantly shorter than the detector deadtime, as a result of which only a tiny fraction of detected events will lead to coincidences. This means that rapid redistribution of radioactivity within the body, which may take place in many investigations, cannot be observed in real time, but only after the fact, since the data needs to be subsequently processed using image reconstruction software.

Scintillation detectors for 140 keV gamma rays normally have thicknesses of 6-12 mm in order to ensure adequate sensitivity. Intrinsic spatial resolution and detector sensitivity, however, have conflicting thickness requirements, since the greater the detector's thickness, the greater the divergence of the scintillation light that emerges on the PMT side. Detector sensitivity therefore needs to be enhanced in other ways if intrinsic resolution is not to be degraded. A 7.5-mm thick NaI detector for 140 keV gamma rays will have an intrinsic resolution of 7.2 mm for planar imaging and SPECT. BGO detectors for 511-keV gamma rays typically have 20-30 mm thicknesses to have adequate detection efficiency, and a continuous BGO detector of 30 mm thickness would have an intrinsic resolution of 31 mm, which would be unacceptable. State-of-the-art PET scanners therefore achieve 4-6 mm spatial resolution by employing 2.54×2.54 cm$^2$ blocks of BGO segmented into 8×8 arrays of (3×3 mm$^2$) elements by means of saw-cuts. The saw-cuts between segments are silvered to help prevent divergence of the scintillation light as it emerges. Further improvement of spatial resolution would require greater reduction of the segment size, which would make it progressively more difficult to identify individual segments within the detector. Experts in the field estimate that 2-mm isotropic resolution using this method would be the limit. However, theoretical analysis of the dependence of resolution on crystal geometry indicates that even this would be impractical.

Although detector block segmentation is effective in restricting divergence of the scintillation light once an interaction in a segment has taken place, it has no effect on the ability of obliquely incident gamma rays to penetrate the detector segments. Image distortion due to gamma rays penetrating the detector segments, or DOI error, requires detector technology that involves either multiple layers of scintillator or the use of avalanche photodiodes (APDs) as photodetectors along with the PMTs, which increases both detector cost and complexity without improving resolution. Although positron tomographs with correction for DOI errors are becoming available, improvement in image quality has only been marginal. Current strategies to overcome the limitations of nuclear imaging systems can be regarded as treating the symptoms, instead of curing the disease itself. Modern PET scanners are also being provided with TOF capability to limit image noise arising from the backprojection of data for image reconstruction. Image quality in nuclear imaging, nevertheless, remains significantly inferior to those of CT and MRI. Currently available detector architecture is unlikely to address the problem in any significant manner. Moreover, despite the large numbers of publications and patents awarded for the improvement of sensitivity in nuclear imaging systems, little attention has been devoted to improving the spatial resolution of nuclear images. It is also to be noted that identification of valid coincidences in current PET systems is often carried out using software operating on large quantities of raw data as opposed to real-time validation using hardware, which leads to an inefficient use of storage space and computing time.

A direct approach to achieving multi-zone operation has been the division of the detector into multiple independent geographical zones, as is the case with pixellated arrays of NaI(Tl) and CsI(Tl) scintillators, for instance. Discrete detectors in these arrays, however, require independent readout using Si photodiodes, which makes them expensive due to their large numbers. Such arrays find application in compact, mobile cameras and pulse-height spectrometry systems.

Semiconductor detector arrays of high purity germanium (HPGe) and ZnCdTe, which eliminate the need for a scintillator-photodetector combination, have also been developed with varying degrees of success. HPGe detectors require cryogenic cooling, however, while ZnCdTe detectors are currently too difficult to fabricate in large sizes. As a result, despite its low quantum efficiency, unit-to-unit variations in quantum efficiency, and poor packing fraction from the dead zone due to the glass walls, the PMT still remains the photodetector of choice in nuclear imaging systems.

In view of the foregoing, there is a definite need for for a new approach to detector design to improve sensitivity, increase image SNR and spatial resolution. Lesion detectability in images needs to be further improved by reducing/eliminating blurring due misplaced pileup events in planar and tomographic imaging alike, and reducing DOI error in PET systems. It is the objective of the present invention to provide all these improvements.

BRIEF DESCRIPTION OF THE DRAWINGS

The present invention is illustrated by way of example, and not by way of limitation, in the figures of the accompanying drawings and in which like reference numerals refer to similar elements and in which.

Unless otherwise indicated illustrations in the figures are not necessarily drawn to scale.

DETAILED DESCRIPTION OF THE PREFERRED EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The present invention will now be described in detail with reference to embodiments thereof as illustrated in the accompanying drawings.

Detailed descriptions of the preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

The three broad design objectives of the preferred embodiment of the present invention are (a) the improvement of detector sensitivity to increase image SNR, (b) the improvement of spatial resolution to increase the detectability of lesions in nuclear images, and (c) the reduction of image blurring due to misplaced pileup events in scintillation camera and SPECT images and DOI error in PET images. This is achieved by significantly reducing detector deadtime using multi-zone detector architecture (MZDA) and including misplaced pileup suppression (MPS) circuitry. Whereas the basic nuclear imaging system builds up an image a single scintillation event per deadtime period, MZDA reduces effective detector deadtime by a factor S, which can be as much as two orders of magnitude ($S \geqq 100$), thereby increasing the peak count rate by a factor of S times. In preferred embodiments of the present invention, using a honeycomb arrangement preferably of 7 PMTs as a detector zone, S can be estimated as $S \approx 11$, where P is the PMT array size. The resulting increase in detector sensitivity obviates the need for thick detectors to improve sensitivity, thereby enabling the spatial resolution to be also improved. Preferred embodiments with MZDA and MPS circuitry generally reduce misplaced events in the image by a factor of P times. In the preferred embodiments, detector sensitivity, which can be made as high as S times if desired, is limited to a factor just two to three times, so that excess sensitivity may be exchanged for improved spatial resolution. The extent, to which S can be increased, in preferred embodiments using MZDA, depends on the minimum PMT size available, currently 1.27 cm (½"). A scintillation camera design, in accordance with the present invention, using a 1.7-cm thick, hexagonal 29-cm wide, NaI(Tl) detector viewed by 331 1.27-cm PMTs will provide a resolution of about 2.1 cm at the collimator face and 3.4 cm at 10 cm from the collimator face, with two times the sensitivity of a single-zone design using the same array size. Designs based on the prior art typically use crystal thicknesses of 0.95 cm to achieve adequate sensitivity, and can provide a resolution of at best 7 cm. Further improvement in sensitivity and spatial resolution is possible only by reducing effective PMT size, since reduction of actual PMT size cannot continue without limit because of the glass walls of the PMTs. In preferred embodiments of the present invention, effective PMT size is reduced by using fiber-optic coupling between the scintillator and the PMTs. In a non-limiting example, a design using a $36 \times 32$ cm$^2$ NaI(Tl) crystal in which the effective size of an array of P=1930 1.27-cm PMTs is reduced to 7.6 mm, using fiber-optic coupling, leads to a resolution of 1.0 cm at the collimator face and 1.8 mm at 10 cm from the collimator face. In the present invention, fiber optic coupling enables the packing fraction of the PMTs to be increased to practically 100% since the thickness of the glass walls no longer constitutes a problem. An additional benefit of fiber optic coupling, in the present invention, is therefore that PMTs can be chosen on the basis of performance and cost alone, irrespective of size and shape.

In accordance with the present invention, a high-resolution/sensitivity hexagonal PET/SPECT scanner using continuous-crystal NaI(Tl) detectors with MZDA, MPS and pileup-prevention circuitry (PPC) shows that the scanner's sensitivity can further be increased by operating three detector pairs simultaneously to triple the coincidence detection rate in PET and to achieve six times the count-rate capability of a single rotating detector head in SPECT imaging. In current PET designs, the spatial (x-, y-, z-) coordinates of valid gamma-ray interactions are first stored in computer memory along with time stamps using a master clock, and the raw data post-processed using software to extract the small fraction of valid coincidences in opposing detector pairs. A significant feature of the present invention is that valid coincidences within the field-of-view (FOV) are identified and time-of-flight (TOF) information determined in real time using hardware, which saves data-processing time. In the present invention, coincidence validation involves pulses of a fixed duration $\tau_c$ being triggered by each valid gamma-ray interaction, and then being compared in real time by the digital circuitry with similar pulses within the FOV to test for valid coincidences. This enables coincidences in each of the three detector pairs to be validated in parallel, thereby increasing the coincidence detection rate of a single detector pair with MZDA by a factor of three times. In the present invention, coincidence events are accepted as valid only if the individual lines of interaction (LOIs) between opposing detector pairs are within the angular FOVs of the detector zones. The angular FOV remains in the range 29° to 34°, as shown in FIG. 4, for a patient of diameter D=30 cm and detectors of length L≈2D≧60 cm in a non-limiting example. Restriction of the LOIs to within the angular FOV, in addition to employing NaI(Tl) to improve energy resolution, minimizes image degradation due to accidental and scatter coincidences from outside the FOV. In a non-limiting example, using a 0.8-mm thick scintillator and an array of P=1287, 1.27-cm PMTs per detector provides a spatial resolution of 0.66 mm and a relative sensitivity of better than 2 times that of single-zone operation, or a resolution of 1.5 mm and a relative sensitivity of better than 10 times, if the crystal thickness is increased to 1.8 mm. In PET, block detector thicknesses of 2-3 cm lead to large DOI errors. In the present invention, image blurring from this source is virtually eliminated on account of the significantly reduced scintillator thicknesses, so that correction of DOI errors is no longer needed. The second major cause of image noise in PET systems is the contribution of random and accidental coincidences to image data. In a non-limiting example, a PET design uses a hexagonal arrangement of continuous flat NaI(Tl) crystals as the detectors. Since NaI(Tl) has significantly higher light output than most other scintillators, this enables an energy window of ±10% to be employed, as compared to ±20% for BGO, for instance. The reduced energy window leads to substantial reduction in the scatter and random coincidences added to the image and therefore an increase in the SNR. In other embodiments of the present invention, the NaI(Tl) detectors can be replaced with those of a suitably fast scintillator, such as, but not limited to, LSO, LYSO, GSO, etc., if time-of-flight (TOF, or TF) capability is desired.

In a preferred embodiment of the present invention, a PET scanner based on the 0.8-mm thick NaI(Tl) scintillators can also be employed as a SPECT scanner with the addition of matching low-energy high-resolution collimators. In non-limiting example, the six detectors are designed to operate independently alongside of each other. The resolution of the scanner is reduced to 0.95 mm at the collimator face and to 1.6 mm at 10 cm from the collimator face, the relative sensitivity being 6.0 times that of a single rotating detector head operating in single-zone mode. A decrease of collimator thickness to get a reduced resolution of 2.0 mm at 10 cm from the collimator face improves the relative sensitivity to 17, as compared to just the 6.0 times of a single detector head. The SPECT scanner can additionally be employed for planar imaging if held stationary during imaging. In this embodiment, each pair of opposing detector heads can be operated back-to-back to acquire three high quality images oriented at angles of 60° to one another. Spatial resolution remains the same as for SPECT imaging, while the sensitivities of the three detector pairs will be one-third that for SPECT operation. In prior art designs, resolution in the planar images normally decreases progressively on moving away from the collimator. In the present invention with two opposing detectors operating back-to-back, the resolution of planar images decreases only on going toward the scanner axis, which leads to significantly better image quality.

In various embodiments of the present invention, the implementation of MZDA need not be limited to single-crystal detectors as discussed above. Detector zones in continuous-crystal designs are needed because of the large size and poor spatial resolution of PMTs used as the photodetectors. Detector zones permit the spatial coordinates of scintillation events to be determined using Anger positioning logic. Pixellated scintillator arrays for compact mobile cameras and semiconductor detector arrays for energy-selective radiation counting are of sufficiently small size to provide high resolution, and are therefore provided with their own dedicated amplifiers and ADCs, which makes them particularly expensive. Counter systems in which the count-rate density is much less than the pixel density can be redesigned to benefit from MZDA, in accordance with the present invention, in which groups of the detectors can share signal-processing circuitry, thereby offering a more economical design that retains the original spatial resolution. In a non-limiting example, the detector density is $N_0$ (pixels/cm$^2$) and the expected maximum count-rate density for the application is $C_0$ (counts/s/cm$^2$), where $C_0 < N_0$. The true count rate $C_0$ can be recorded with no more than 20% deadtime losses, provided that $C_0 > 0.223/\tau_0$, where $\tau_0$ is the deadtime of a single detector in the pixel matrix operating independently, which means that $S = 4.48C_0$. Amplifiers and event-validation circuitry in a pixellated detector can then be shared between two or more adjacent pixels provided that $k = N_0/S \geq 2$, or $N_0 > 2S = 8.96C_0 26\ 9.0C_0$. If $2 \leq k < 3$, two adjacent pixels can share the same circuitry, since at most only one event on average arrives at each pixel pair. Similarly, if $3 \leq k < 4$, three adjacent pixels can share the circuitry, and so on. The electrical signals generated in the shared signal-processing circuitry are easily decoded for event position within the pixel matrix, while the energy of the gamma rays is determined from the digital values of these signals. The ability to share the circuitry between multiple pixels enables the pixels to be made sufficiently small for good spatial resolution while reducing the circuit cost by a factor of k times.

Figures 1A, 1B, 1D:
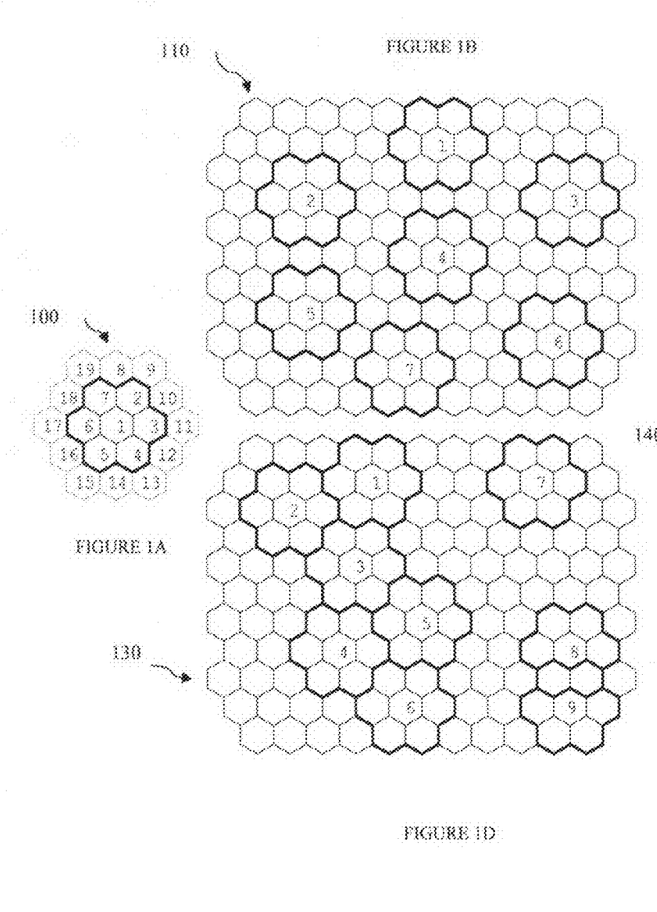
FIGS. 1A-1E illustrate exemplary PMT array structures for detector zones in accordance with embodiments of the present invention.
Figure 1C:
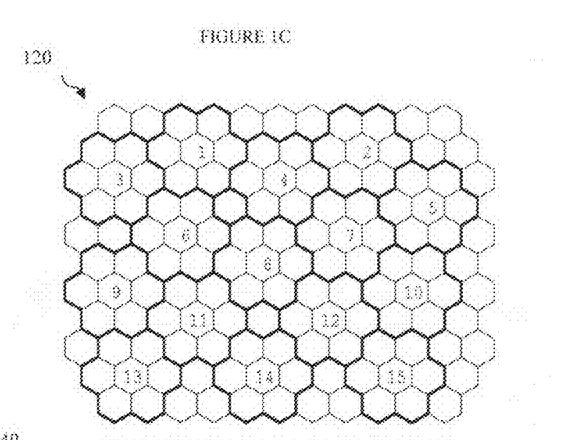
Figure 1E:
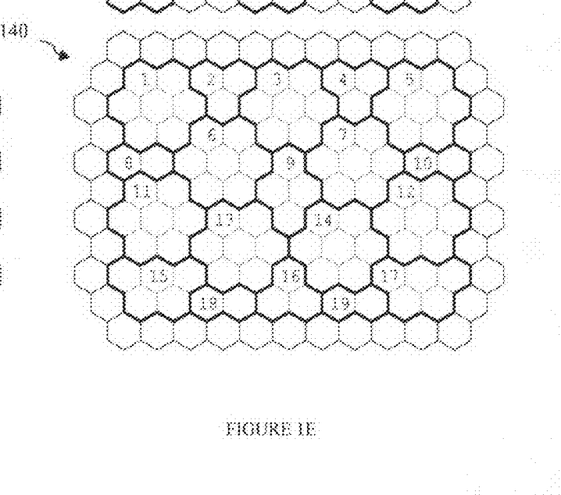

FIGS. 1A-1E illustrate exemplary PMT array structures in accordance with embodiments of the present invention. FIG. 1A depicts an exemplary PMT array 100 with a honeycomb structure to make detector zones that consist of groups of seven PMTs. The seven PMTs 1-7 provide sufficient information for accurate energy and position signals for the detected event to be generated. Analysis shows that, when a valid event is detected at the central PMT 1, the seven closest PMTs collect between 90% and 96% of the scintillation light, and that cross-talk between two adjacent detector zones is less than 1%. FIG. 1B depicts the lowest maximum number of 7 independent detector zones for the array 110 of 132 PMTs shown, while FIG. 1C shows the highest maximum number of 15 of independent detector zones in array 120, depending on event distribution. The number of independent detector zones is a maximum when no new ones can be added without causing an overlap. FIG. 1D illustrates that detector zones can be tightly packed together in array 130, like zones 1 to 6, completely isolated, like zone 7, or overlapping spatially, like zones 8 and 9, which will be rejected by the detector-zone circuitry. FIG. 1E illustrates PMTs around the outside of the array 140 cannot become central PMTs to detector zones because there will then be fewer than seven PMTs in the detector zones. Possible central PMTs to detector zones can be grouped together to share detector zone circuitry since no two PMTs separated by less than two intervening PMTs can be central PMTs to independent detector zones. The PMTs of a detector zone obviously meet this criterion, and the maximum number of central PMTs that can share detector-zone circuitry is therefore also seven. The number F of detector-zone circuitries needed can be minimized by maximizing the number of sharing groups consisting of seven central PMTs. Circuits for groups of central PMTs sharing detector zones can come in modular form with the modules consisting of groups 2 to 7 PMTs. Any PMT array can be formed by joining F such modules together. The F=19 groups of central PMTs for the array in this example are made up of modules consisting of 2 to 7 PMTs, although a module with 6 PMTs was not needed.

Figure 2A:
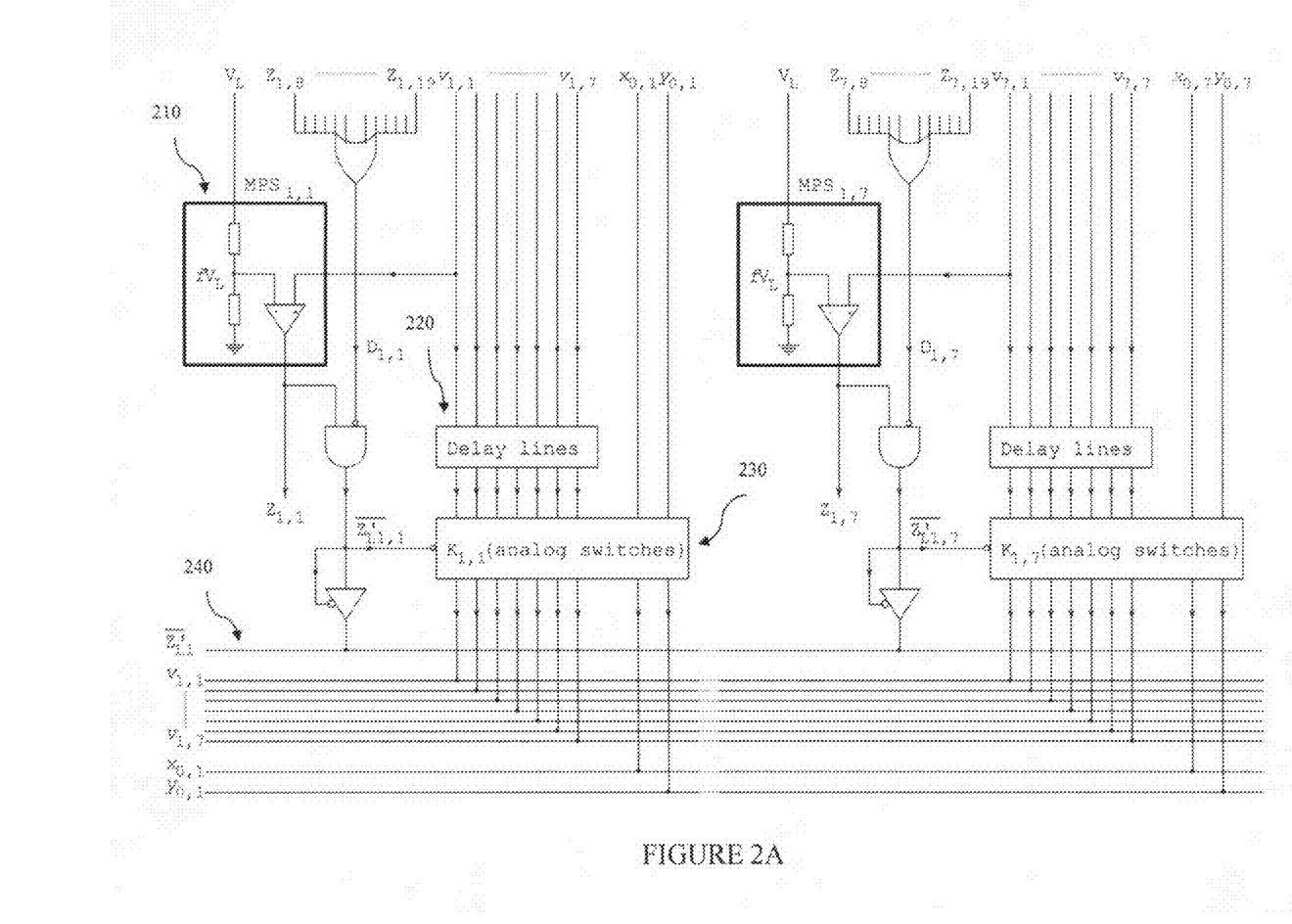
FIG. 2A illustrates a simplified block diagram of exemplary misplaced pile-up suppression circuitry for detector zones in accordance with an embodiment of the present invention.

FIG. 2A illustrates a simplified block diagram of exemplary misplaced pile-up suppression circuitry in accordance with an embodiment of the present invention. FIG. 2A shows misplaced pile-up suppression (MPS) circuitry 210 and event switches 230 for a group of 7 central PMTs sharing detector-zone circuitry, since the detector-zone circuitry ensures that just one central PMT at a time is active. The function of the MPS circuitry 210 is to reject preamplifier (PA) outputs of the central PMT that are due to scattered radiation. The PA outputs of the 12 PMTs closest to the detector zone are also checked to prevent pileup events and to minimize cross-talk between adjacent detector zones. FIG. 2A shows one implementation of the MPS circuitry 210 for PMTs $T_1$ through $T_7$, which comprise the first group of central PMTs for sharing detector-zone circuitries. The spatial coordinates $(x_{0,1}, y_{0,1})$ of $T_1$ with respect to the crystal center and the PA outputs $(v_{1,1}, \ldots, v_{1,7})$ of the PMTs within the detector zone are taken to the common bus 240 through the set of analog switches 230. The associated delay lines 220 allow time for $\overline{Z'_{L1}}$ to be generated and the switches to be activated. The MPS circuitry 210 for $T_1$ generates the logic-high pulse $Z_{1,1}$, when $v_{1,1} > f_{min} V_L$, which also means that $v_{1,1} > v_{1,i}$, $i = 2, 3, \ldots, 7$ and that the detected event may be valid. The event at $T_1$ is determined to be spatially independent if no event in the 12 second-ring PMTs at the same time satisfies the condition $v_{1,i} > f_{min} V_L$, $i = 8, 9, \ldots, 19$, which leads to both being rejected. The closest that a second valid event can be to that at $T_1$ is in one of the 18 third-ring PMTs, as for the central PMTs of the detector zones 1, 2 and 3 in FIG. 1D. When the PA outputs of the second-ring PMTs meet the above requirement, $D_{1,1} = 0$ and $\overline{Z'_{L1,1}}$, so that $\overline{Z'_{L1,1}}$ closes the analog switches 230 and also appears as $\overline{Z'_{L1}}$ in the common bus 240. Other PMTs in the same group as $T_1$ will not be connected to this bus, since only one central PMT at a time can be present.

Figure 2B:
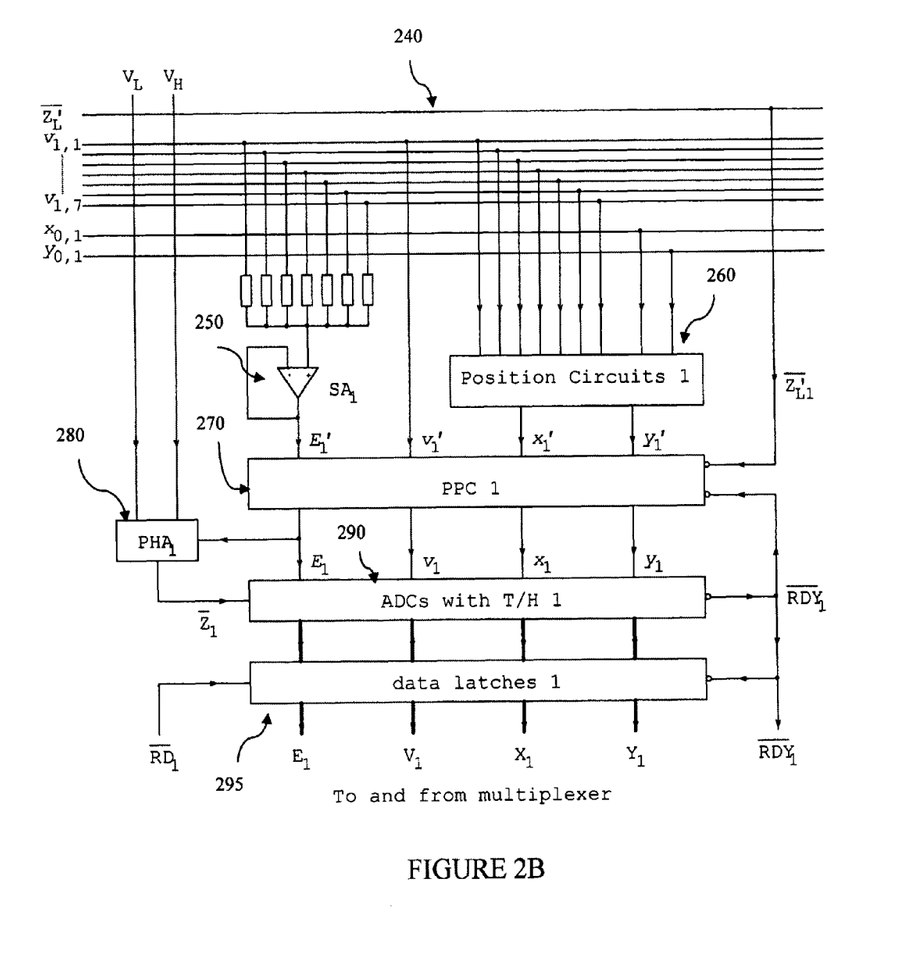
FIG. 2B illustrates a simplified block diagram of exemplary detector-zone circuitry in accordance with an embodiment of the present invention.
Figure 3:
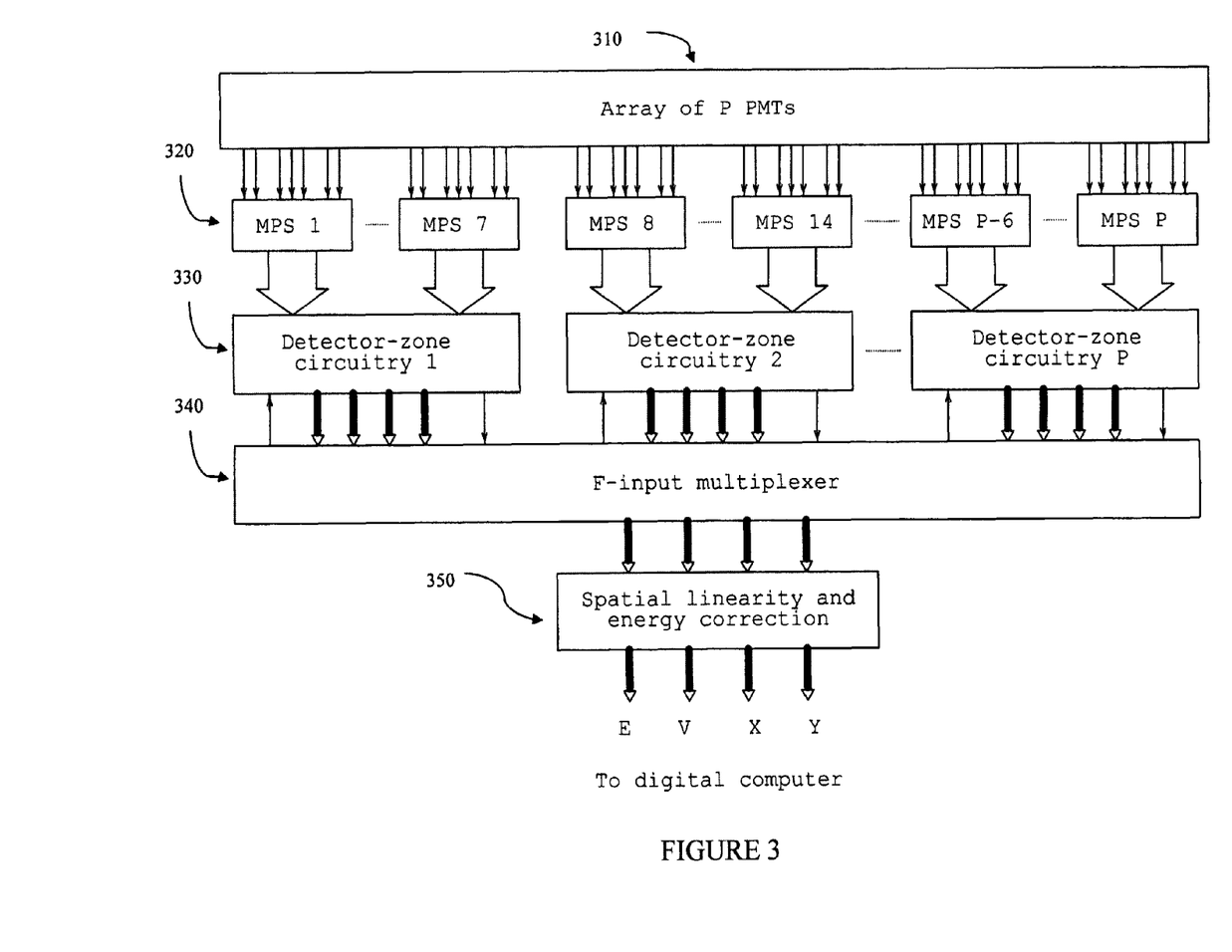
FIG. 3 illustrates a simplified block diagram of an exemplary scintillation camera with MZDA in accordance with an embodiment of the present invention.

FIG. 2B illustrates a simplified block diagram of exemplary detector-zone circuitry in accordance with an embodiment of the present invention. The detector-zone circuitry includes a summing amplifier (SA) 250, Anger position circuitry 260, pileup prevention circuitry (PPC) 270, a pulse-height analyzer (PHA) 280 with a wider than standard energy window, a set of 4 ADCs with T/H 290 and external data latches 295. A wider than standard energy window is used here to make subsequent energy correction possible as indicated in FIG. 3. The PA outputs of the PMTs in the detector zone, the coordinates $(x_{0,1}, y_{0,1})$ of the center of $T_1$, and the digital signal $\overline{Z'_L}$ are available on the common bus 240 at the top of the figure. The analog position circuitry 260 generates the coordinates $\Delta x$ and $\Delta y$ of the interaction point with respect to the center of $T_1$, so that the absolute coordinates $x'_1 = x_{0,1} + \Delta x$ and $y'_1 = y_{0,1} + \Delta y$ of the interaction point with respect to the crystal center can be generated. The energy signal $E'_1$ is likewise generated in the SA 250 from the PA outputs within the detector zone. The analog signals generated are applied to the PPC 270 to recover the first pulse from multiple-pileup interactions. The corrected energy signal $E_1$ is tested to determine whether or not $V_L < E_1 < V_H$, in which case a logic-low pulse $\overline{Z_1}$ will be generated that initiates digitization at the ADCs 290. The digital outputs of the ADCs are held in external data latches 295 and read sequentially into the computer interface through an F-input multiplexer.

FIG. 3 illustrates a simplified block diagram of an exemplary scintillation camera with MZDA in accordance with an embodiment of the present invention. The P PMTs of the array 310 are divided into F nearly equal groups to share F detector-zone circuitries 330. Up to F independent events can therefore be detected, the digital values of the energy and position signals then being held in data latches 295, FIG. 2, until read into computer memory through a high-speed multiplexer 340. The multiplexer reads the F number of data latches once every deadtime period to ensure that the computer interface keeps in step with the multi-zone detector. At the top is the array 310 of P PMTs, each provided with an MPS circuitry 320. The PMTs in the array are arranged into F groups of 5 to 7 central PMTs to share detector-zone circuitries. The PA outputs of those central PMTs for which $v_1 > f_{min} V_L$ are applied to the detector-zone circuitries 330 to generate the energy and position signals for the detected events. These signals are then applied to the PPC 270 to recover the first event in pileup interactions that would otherwise be rejected by the PHA 280, the PPC thus helping to reduce detector deadtime. The energy signals are then applied to the PHAs 280 for energy discrimination, after which the analog signals from the detector zones are applied to their respective ADCs 290 for digitization. The digital data from the ADCs are applied to the computer interface through an F-input multiplexer 340. Spatial linearity and energy correction 350 are then applied to the data before transfer to computer memory for image display and data analysis. Spatial linearity correction in the image is needed to remove distortion arising from nonlinearities in the analog positioning circuitry, inequalities in the gains of the PAs of PMTs within the detector zones, and from imperfections in the detector crystal and the collimator. Linearity correction involves assigning a correction term for the position coordinates of each pixel in the image. Likewise, energy correction in the image is needed to minimize errors in the energy signals arising from inequalities in the gains of the PAs in the detector zones. As correction involves either an increase or decrease in $E_1$ for each event, most energy signals within the provisional window of the PHA 280 will be retained, while some at both ends of the window will be discarded in accordance with the lookup table. Errors in event energy are minimized by maintaining a regular quality control procedure that ensures that the gains of the PAs of PMTs remain as nearly equal as possible.

Figure 4A:
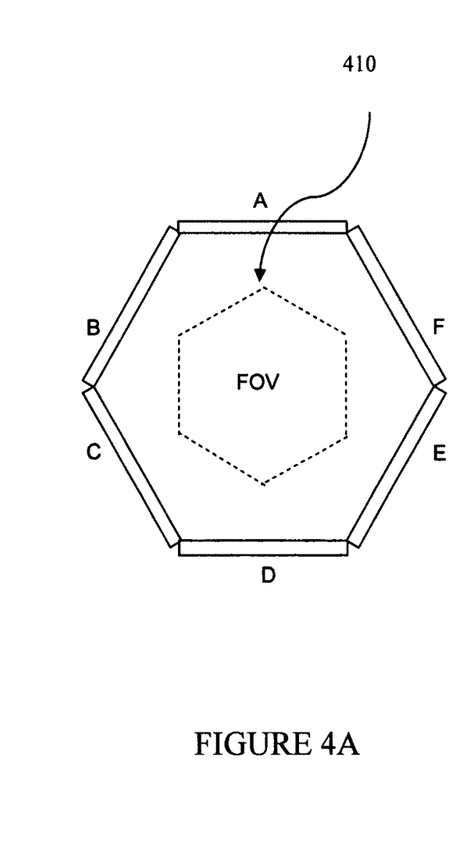
FIG. 4A illustrates a maximum usable field-of-view (FOV) for a hexagonal PET scanner in accordance with an embodiment of the present invention.
Figure 4B:
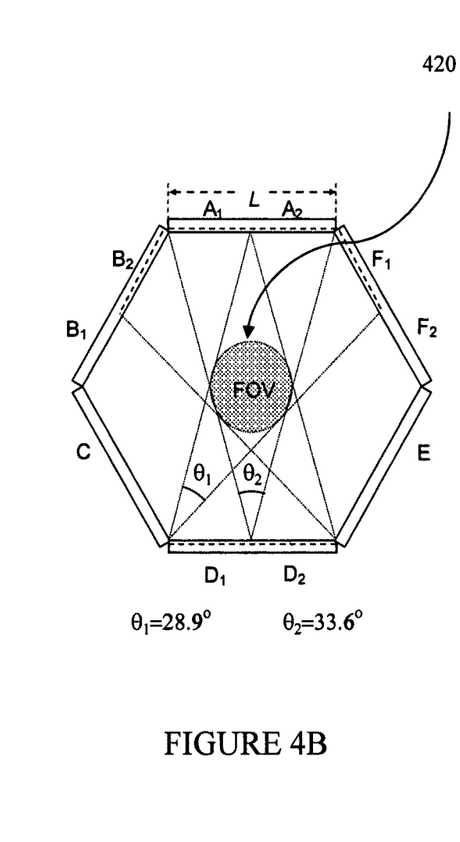
FIG. 4B illustrates a minimum circular field-of-view (FOV) for a hexagonal PET scanner in accordance with an embodiment of the present invention.
Figure 4C:
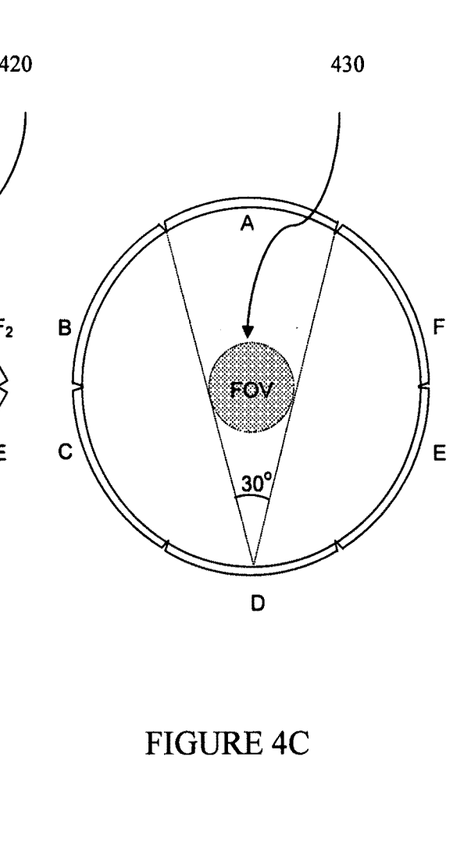
FIG. 4C illustrates a minimum circular field-of-view (FOV) for a hexagonal PET scanner based on curved detectors in accordance with an embodiment of the present invention.

FIG. 4A illustrates a maximum usable field-of-view (FOV) for a PET scanner employing six flat rectangular NaI(Tl) detectors in accordance with an embodiment of the present invention. The maximum FOV 410 is the hexagonal area viewed by the six detectors A-F. FIG. 4B illustrates a minimum circular field-of-view (FOV) for a PET scanner in accordance with an embodiment of the present invention. For a minimum circular FOV 420 of diameter D=L/2 (shaded), the angular aperture for a PMT varies from 28.9° at the corners to 33.6° at the centers of detectors A-F. FIG. 4C illustrates a minimum circular field-of-view (FOV) for a PET scanner with six curved detectors in accordance with an embodiment of the present invention. For a minimum circular FOV 430 of diameter D=L/2 (shaded), the angular aperture for a PMT is uniformly equal to 30° for all PMTs in the six detectors. For an FOV of diameter D=L/2, each PMT in one detector can be in coincidence with the P PMTs in within its angular FOV in opposing detectors. Limiting coincidence detection to within the minimum FOV minimizes image noise due to scatter and random coincidences.

Figure 5:
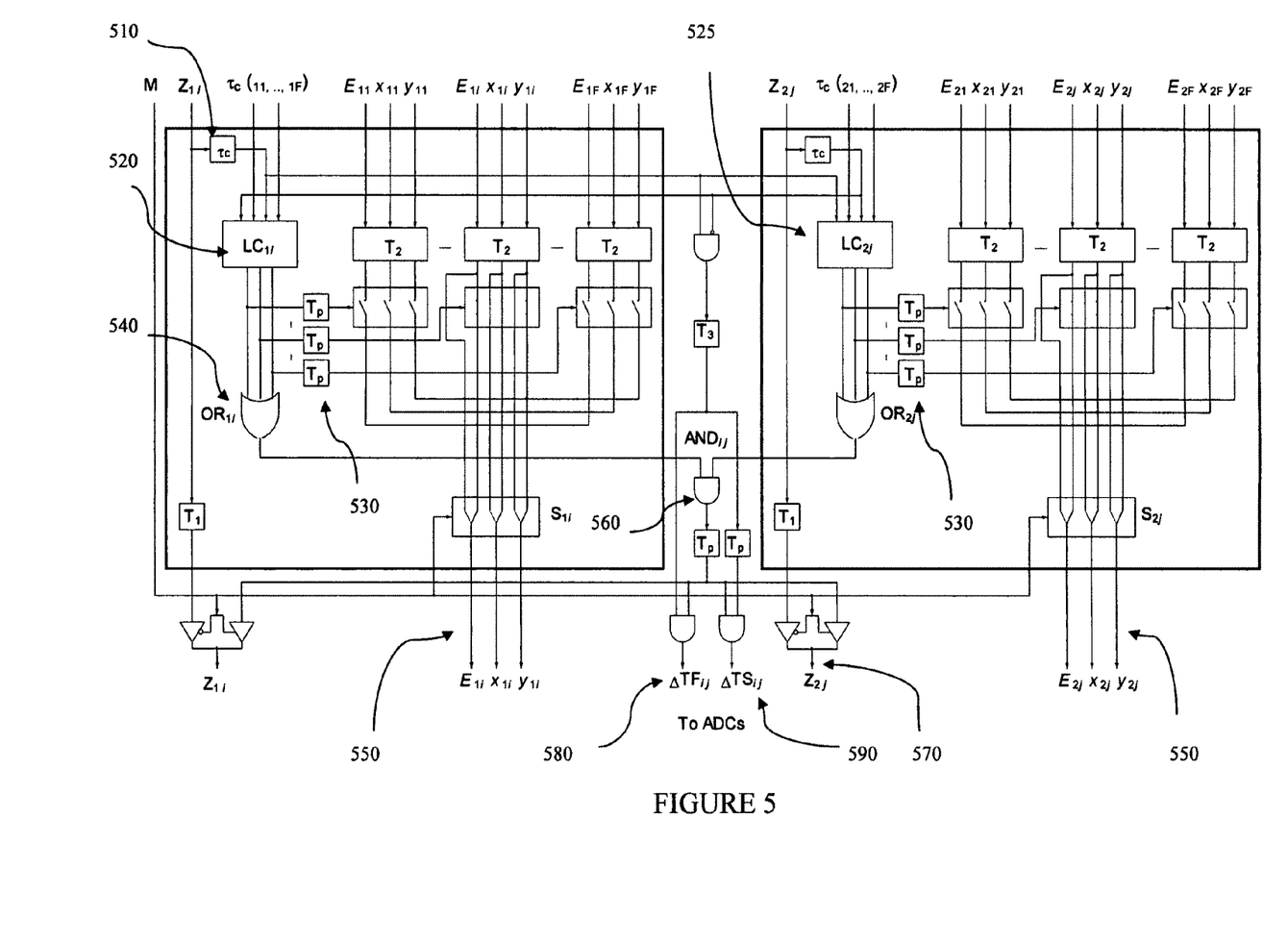
FIG. 5 illustrates exemplary coincidence validation logic circuitry for a PET/SPECT scanner in accordance with an embodiment of the present invention.
Figure 6:
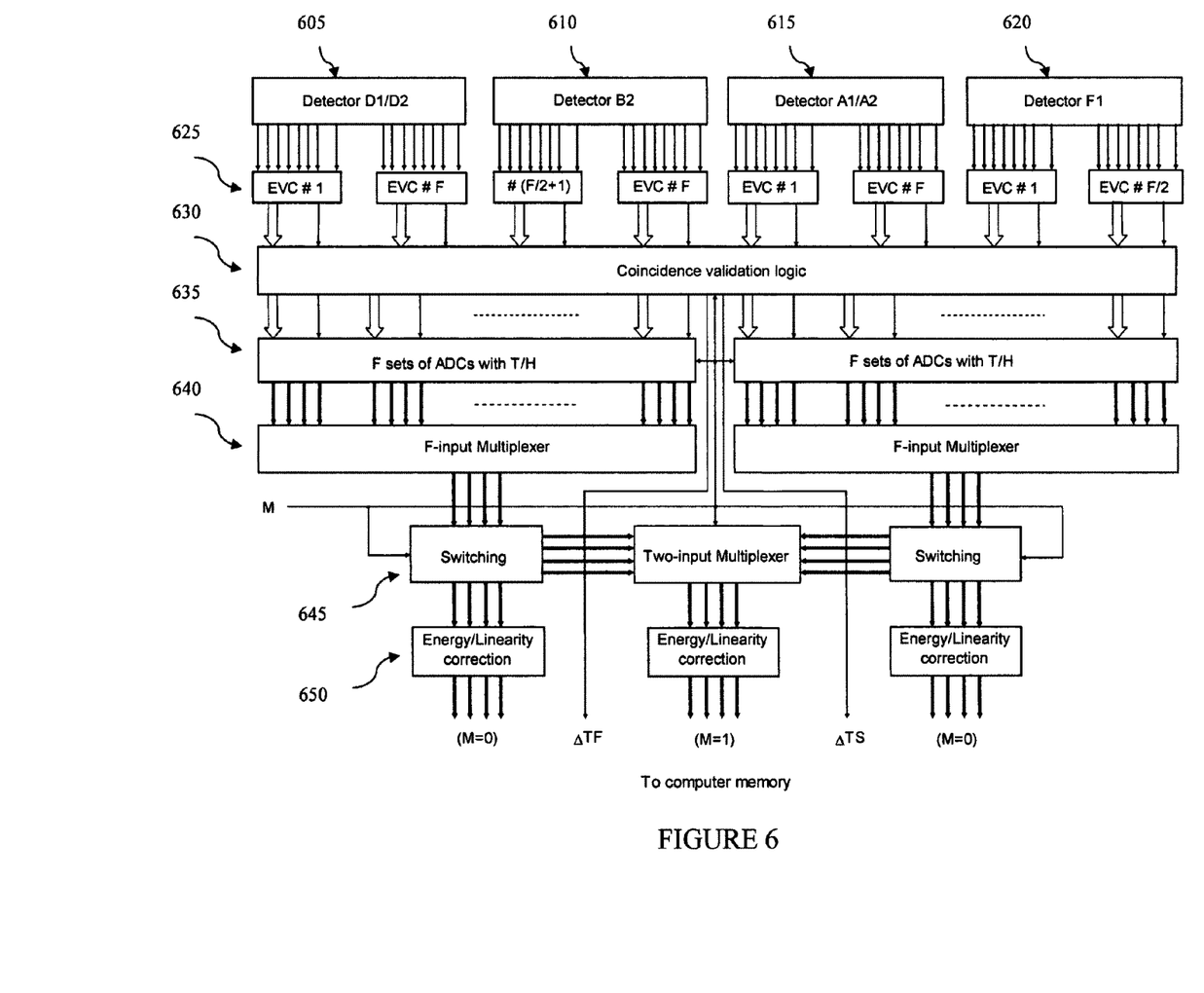
FIG. 6 illustrates a simplified functional block diagram of an exemplary hexagonal PET/SPECT scanner in accordance with an embodiment of the present invention.

FIG. 5 illustrates exemplary coincidence validation logic circuitry for a PET/SPECT scanner in accordance with an embodiment of the present invention. Each detector zone in one detector can have coincidences with F other detector zones within its angular FOV. The logic level signal Z and the analog signals E, x and y are taken from the PHA 280 and the energy and position circuitry 260, respectively, as shown in FIG. 2B. The signals labeled with the subscripts $1i$ and $2j$ ($1 \leq i \leq F$, $1 \leq j \leq F$) correspond to detector zone i in detector 1 and to detector zone j in detector 2, respectively. Z-signals from valid interactions in either detector trigger the generation of narrow pulses of duration $\tau_c$ 510 where $2\tau_c$ is the resolution, or coincidence time window, of the scanner. The $\tau_c$ pulse due to, say, event U from detector zone $1i$ is compared in the logic circuitry block ($LC_{2j}$) 525 with the $\tau_c$ pulse 510 of every detector zone $2j$, and if a valid coincidence with just one event, say V, in detector zone $2j$ is detected, a logic-high pulse is presented at the corresponding output terminal in the $LC_{2j}$ block 525. This logic-high pulse triggers a pulse of duration $T_p$ 530, which is then used to connect the energy and position signals in detector zone $2j$ to the common output bus 550. The narrow logic high pulse from $LC_{2j}$ 525 also appears at the $OR_{2j}$ 545 output. Since it is possible for V in detector zone $2j$ to be also in coincidence with an event W in detector 1, in addition to event U, or with events in other detectors within the FOV of detector 2, the block $LC_{1i}$ 520 is used to ensure that a valid coincidence is limited to just event U in detector zone $1i$. The gate $AND_{ij}$ 560 has a logic high output only for a two-way coincidence between V and U in detectors 2 and 1, thus ruling out a three-way coincidence with other events. When this is the case, and suitably fast scintillators are being employed, the coincidence validation circuitry can also be used to generate an output pulse $\Delta TF_{ij}$ with duration $\tau_c + \Delta TF_{ij}$, where $\Delta TF_{ij}$ is the difference between the flight times of gamma rays $1i$ and $2j$. $TFP_{ij}$ has duration $\tau_c$ if $\Delta TF_{ij}=0$ and duration $2\tau_c$ if $\Delta TF_{ij}=\tau_c$. The narrow logic-high pulse from $AND_{ij}$ 560 is used to generate a pulse of width $T_p$ 570. The pulse $\Delta TF_{ij}$ 580 is at logic level 0 when there is no valid coincidence. When there is coincidence and $\Delta TF_{ij}$ is at logic 1, the logic level of the $\Delta TS_{ij}$ 590 shows whether or not gamma ray $1i$ leads ($\Delta TS_{ij}=1$) or lags ($\Delta TS_{ij}=0$) gamma ray $2j$. The energy and position signals of event V in detector zone $2j$ are presented as outputs $E_{2j}$, $x_{2j}$ and $y_{2j}$, respectively, while the pulse of width $T_p$ replaces $Z_{2j}$ at the output, as shown in the figure for M=1. When operation is in SPECT mode, or M=0, the signals $Z_{2j}$, $x_{2j}$ and $y_{2j}$ in detector zone $2j$ are passed on to the outputs without modification. While FIG. 5 shows only two blocks $1i$ and $2j$, it should be kept in mind that i and j are variables ($1 \leq i \leq F$, $1 \leq j \leq F$) as noted earlier, and, in fact, F blocks on either side are being represented. When operation is in PET mode, the four lower switches in the figure ensure that events in the detector 2 are arranged in the same order as related coincidence events in detector 1, enabling coincident signals in the two detectors to be applied to corresponding ADC sets in the opposing detectors. The digitized values in the data latches can be read concurrently through the two F-input multiplexers, and then consecutively by the two-input multiplexer, as indicated in FIG. 6. The x- and y-coordinates of coincident events may even be read into computer memory as single words to facilitate data backprojection and subsequent image reconstruction.

FIG. 6 illustrates a simplified functional block diagram of an exemplary hexagonal PET/SPECT scanner in accordance with an embodiment of the present invention. The scanner operation is in SPECT mode if M=0 is chosen and in PET mode if the coincidence validation circuitry (CVC) in FIG. 5 is activated by choosing M=1. The coincidence validation circuitries CVC #1 through CVC #F 625, where F is as defined in above, include detector-zone circuitry up to and including the PHA 280 in FIG. 2B. In PET mode, detector D can have coincidences with the detector halves B2, A1, A2 and F1 in FIG. 4B. A detector zone along the boundary of the detector halves D1 and D2 can have valid coincidences only with the detector halves A1 and A2. A detector zone at the far left of detector D1 can have valid coincidences with the detector halves A2 and F1, whereas a detector zone at the far right of D2 can have valid coincidences with the detector halves B2 and A1. In general a detector zone anywhere in the scanner can have valid coincidences with the equivalent of at most two detector halves, which means with F detector zones. Coincidence validation circuitry (CVC) 630 is provided to ensure that only two-way coincidences with these detector zones are accepted and that coincidences from outside of the FOV are discarded to minimize scatter and accidental coincidences. TOF capability can be added to the PET scanner provided that a suitably fast scintillator replaces the NaI(Tl).

Figure 7A:
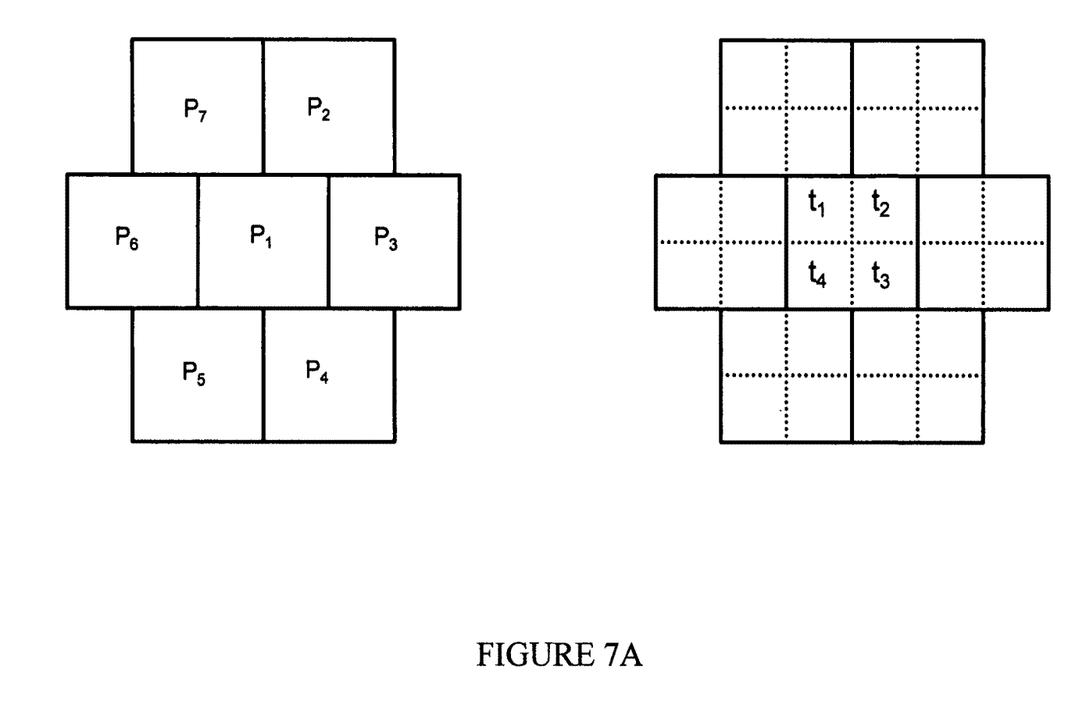
FIG. 7A illustrates exemplary geometric sampling employing a larger number of reduced effective-size PMTs by using fiber-optic coupling in accordance with an embodiment of the present invention.
Figure 7B:
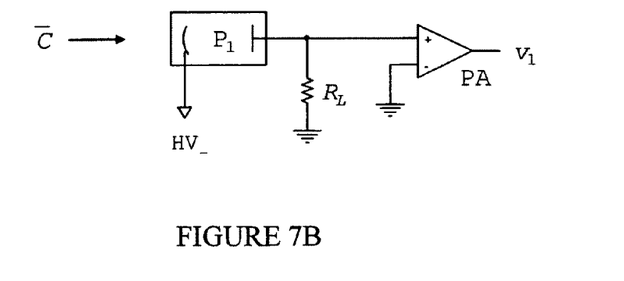
FIG. 7B illustrates an exemplary equivalent circuit of PMT $P_1$ and its PA in FIG. 7A in accordance with an embodiment of the present invention.
Figure 7C:
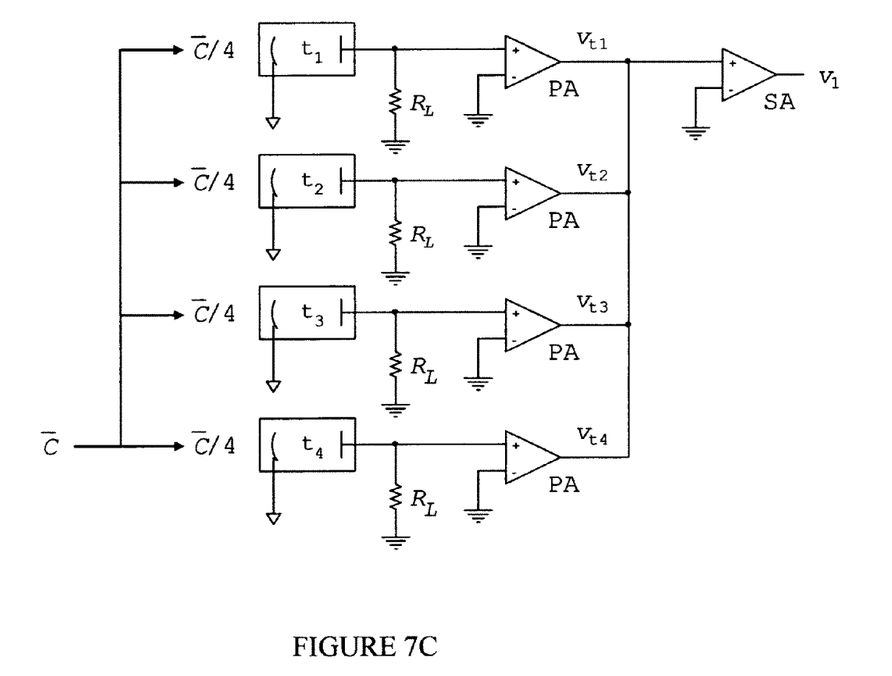
FIG. 7C illustrates an exemplary equivalent circuit of a four-channel PMT, associated PAs and SA in accordance with an embodiment of the present invention.

FIG. 7A illustrates exemplary geometric sampling employing a larger number of reduced effective size PMTs by using fiber-optic coupling in accordance with an embodiment of the present invention. Each of the regular PMTs $P_1$-$P_4$ in the detector zone is replaced by four PMTs $t_1 4_4$, or a four-channel PMT of reduced effective size by using fiber-optic coupling. FIG. 7B illustrates an exemplary equivalent circuit of PMT $P_1$ in FIG. 7A and its PA in accordance with an embodiment of the present invention. FIG. 7C illustrates an exemplary equivalent circuit of a four-channel PMT, and associated PAs and SA in accordance with an embodiment of the present invention. Dividing the scintillation light applied to one PMT equally between two or more PMTs also reduces nonlinear distortion due to $P_1$ and the PA, since the four-channel PMT and the PAs now operate in their more linear ranges. Although the optical fibers are shown to have rectangular terminations in FIG. 7A, the terminations are ideally hexagonal on the scintillator side, and of the same shape as the PMTs on the PMT side.

Figure 8:
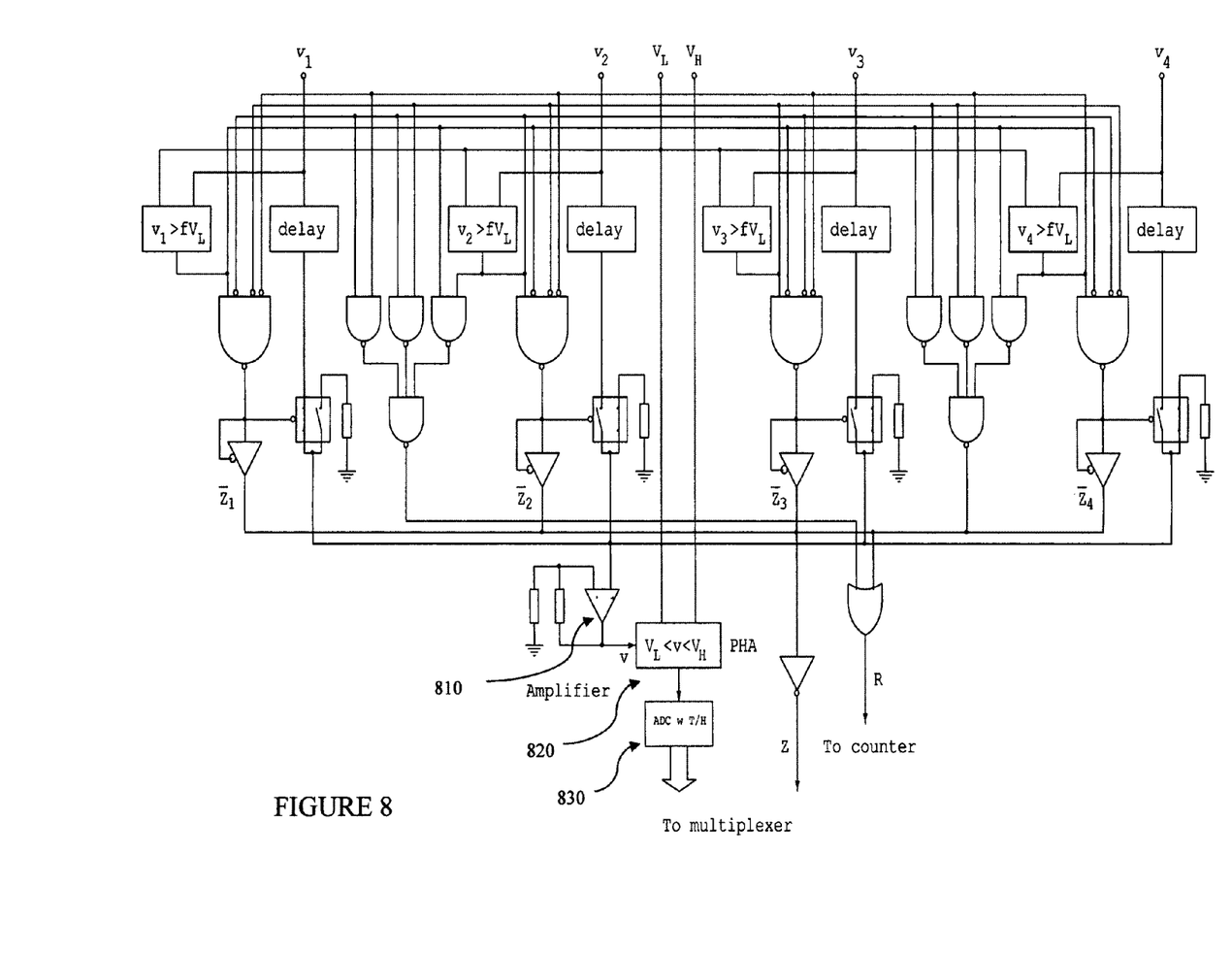
FIG. 8 illustrates an exemplary circuit enabling four adjacent radiation counters to share an amplifier, PHA and ADC in accordance with an embodiment of the present invention.

FIG. 8 illustrates an exemplary circuit for four radiation counters, say $t_1$ through $t_4$, also arranged as in FIG. 7A, in accordance with an embodiment of the present invention. Outputs $v_1$ through $v_4$ of the counters share an amplifier 810, a PHA 820, and an ADC 830. A logic high Z pulse is generated each time a valid particle or photon is detected. The switch positions shown are for the case when a valid signal $v_1$ is present. Coincidence detection leading to more than one valid signal at a time is prevented. Optionally, the circuit can include a provision to generate a logic-high pulse R as shown each time two or more coincident events are being rejected. The count of these pulses can be used to provide statistical information regarding the margin of error with which the total count is recorded.

Having fully described at least one embodiment of the present invention, other equivalent or alternative methods and an apparatus for high resolution/sensitivity and improved image signal-to-noise ratio (SNR) for planar and tomographic (PET/SPECT) imaging according to the present invention will be apparent to those skilled in the art. The invention has been described above by way of illustration, and the specific embodiments disclosed are not intended to limit the invention to the particular forms disclosed. For example, the particular implementation of the scintillation detectors and photodetectors may vary depending upon the particular type nuclear imaging scanner. The circuits described in the foregoing are exemplary and other designs in accordance with the teachings provided herein are contemplated as within the scope of the present invention. Furthermore, the techniques described in the foregoing were directed to nuclear imaging; however, similar techniques may be applied to various other types of scanners, such as in astrophysics, high energy radiation detectors in nuclear physics, etc., and are contemplated as within the scope of the present invention. The invention is thus to cover all modifications, equivalents, and alternatives falling within the spirit and scope of the following claims.

Claim elements and steps herein have been numbered and/or lettered solely as an aid in readability and understanding. As such, the numbering and lettering in itself is not intended to and should not be taken to indicate the ordering of elements and/or steps in the claims.

What is claimed is:

1. A method comprising:
   steps for choosing an optimum detector for producing bursts of optical photons in response to events comprising incident radiation where spatial resolution is increased and a sensitivity is decreased;
   steps for arranging a plurality of photodetectors in a hexagonal array into groups each comprising a honeycomb array for viewing a plurality of zones of said detector and concurrently converting said bursts of optical photons into signal outputs where said sensitivity is effectively increased;
   steps for identifying and rejecting signal outputs that are due to scattered photons of said incident radiation to mitigate blurring;
   steps for simultaneously generating energy and position signals at multiple zones of said detector during one deadtime period where effective detector deadtime is reduced and effective detector sensitivity is increased; and
   steps for transferring said energy and position signals to computer memory for image display and data analysis.

2. The method as recited in claim 1, comprising steps for further reducing said effective detector deadtime of said steps for detecting energy.

3. The method as recited in claim 1, further comprising steps for converting energy and position signals to digital.

4. The method as recited in claim 1, further comprising steps for mitigating distortions arising from device nonlinearities.

5. The method as recited in claim 1, further comprising steps for mitigating errors arising from inequalities in gains of said photodetectors and associated preamplifiers.

6. The method as recited in claim 1, further comprising steps for coupling said bursts of optical photons to said photodetectors for reducing an effective size of said photo detectors.

7. A method comprising steps of:
   detecting energy for producing bursts of optical photons in response to events comprising incident radiation in which a parameter of means for detecting energy being chosen to increase spatial resolution with a decrease in sensitivity;
   arranging a plurality of photodetectors into F number of sharing groups, each of said sharing groups comprising two to seven central groups, each of said central groups comprising seven photodetectors in a honeycomb array for viewing zones of said bursts of optical photons and converting said bursts of optical photons into signal outputs, where each of said central groups is associated with a zone of said energy detecting means and said sensitivity is effectively increased;
   rejecting signal outputs that are due to scattered photons of said incident radiation for each of said central groups to mitigate image blurring;
   generating energy and position signals in detection of F number of said events during one deadtime period for each of said F number of sharing groups where effective deadtime of said energy detecting means is reduced and sensitivity is increased; and
   transferring said energy and position signals of said F number of said events to computer memory for image display and data analysis.

8. The method as recited in claim 7, further comprising the step of further reducing effective detector deadtime using pileup prevention circuitry.

9. The method as recited in claim 7, further comprising the step of converting analog energy and position signals to digital.

10. The method as recited in claim 7, further comprising the step of mitigating distortions arising from device nonlinearities using spatial linearity correction circuitry.

11. The method as recited in claim 7, further comprising the step of mitigating errors arising from inequalities in gains of said photodetectors and associated preamplifiers using energy correction circuitry.

12. The method as recited in claim 7, further comprising the step of coupling said bursts of photons to said photodetectors using fiber-optics for reducing an effective size of said photodetectors.

13. A system comprising:
- at least one continuous energy detector for producing bursts of optical photons in response to events comprising incident radiation, a parameter of said energy detector being chosen to increase spatial resolution with a decrease in sensitivity;
- a multi-zone detector architecture comprising a hexagonal array of a plurality of photodetectors comprising F number of sharing groups, each of said sharing groups comprising two to seven central groups, each of said central groups comprising seven photodetectors arranged in a honeycomb array for viewing zones of said at least one energy detector and converting said bursts of optical photons into signal outputs, where each of said central groups is associated with a zone of said at least one energy detector and said sensitivity is effectively increased;
- a misplaced pile-up suppression circuitry associated with each of said central groups for rejecting signal outputs that are due to scattered photons of said incident radiation to mitigate image blurring;
- a detector-zone circuitry associated with each of said F number of sharing groups for generating energy and position signals in detection of up to F number of said events during one deadtime period where effective deadtime of said energy detector is reduced and sensitivity is increased; and
- a multiplexer with F inputs for transferring said energy and position signals of said F number of said events to computer memory for image display and data analysis.

14. The system as recited in claim 13, further comprising pileup prevention circuitry for further reducing effective deadtime of said at least one energy detector.

15. The system as recited in claim 13, further comprising analog-to-digital converters for said energy and position signals.

16. The system as recited in claim 13, further comprising spatial linearity correction circuitry for mitigating distortions arising from device nonlinearities.

17. The system as recited in claim 13, further comprising energy correction circuitry for mitigating errors arising from inequalities in gains of said photodetectors and preamplifiers.

18. The system as recited in claim 13, further comprising fiber-optic coupling between said at least one energy detector and said photodetectors for reducing an effective size of said photodetectors.

19. The system as recited in claim 18, wherein said fiber-optic coupling at said at least one energy detector comprises a hexagonal shape for maximizing a packing fraction.

20. The system as recited in claim 13, wherein said F number of central groups in each of said F number of sharing groups share said associated detector-zone circuitry.

* * * * *